US010099986B2

(12) United States Patent
Grison et al.

(10) Patent No.: US 10,099,986 B2
(45) Date of Patent: Oct. 16, 2018

(54) HYDROSILANE/LEWIS ACID ADDUCT, PARTICULARLY ALUMINUM, IRON, AND ZINC, METHOD FOR PREPARING SAME, AND USE OF SAID SAME IN REACTIONS FOR REDUCING CARBONYL DERIVATIVES

(71) Applicants: CENTRE NATIONAL DE LA RECHERCHE SCIENTIFIQUE, Paris (FR); UNIVERSITE DE MONTPELLIER, Montpellier (FR)

(72) Inventors: Claude Grison, Castelnau-le-Lez (FR); Vincent Escande, Montpellier (FR)

(73) Assignees: CENTRE NATIONAL DE LA RECHERCHE SCIENTIFIQUE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/547,425

(22) PCT Filed: Jan. 29, 2016

(86) PCT No.: PCT/FR2016/050201
§ 371 (c)(1),
(2) Date: Jul. 28, 2017

(87) PCT Pub. No.: WO2016/120574
PCT Pub. Date: Aug. 4, 2016

(65) Prior Publication Data
US 2018/0009730 A1 Jan. 11, 2018

(30) Foreign Application Priority Data

Jan. 30, 2015 (FR) ...................................... 15 00177
Apr. 8, 2015 (FR) ...................................... 15 53031
May 5, 2015 (FR) ...................................... 15 54042

(51) Int. Cl.
*C07C 45/65* (2006.01)
*C01F 7/00* (2006.01)
*C01G 9/00* (2006.01)
*C01G 49/10* (2006.01)
*C07C 45/62* (2006.01)
*C07C 29/17* (2006.01)
*C07C 29/143* (2006.01)
*C01F 7/56* (2006.01)
*C01G 9/04* (2006.01)
*C07F 7/08* (2006.01)

(52) U.S. Cl.
CPC ................ *C07C 45/65* (2013.01); *C01F 7/56* (2013.01); *C01G 9/04* (2013.01); *C01G 49/10* (2013.01); *C07C 29/143* (2013.01); *C07C 29/175* (2013.01); *C07C 45/62* (2013.01); *C07F 7/0896* (2013.01); *C07C 2601/08* (2017.05); *C07C 2601/14* (2017.05)

(58) Field of Classification Search
CPC C07C 45/65; C01G 9/04; C01G 49/10; C01F 7/56
See application file for complete search history.

(56) References Cited

U.S. PATENT DOCUMENTS 6,589,644 B1 7/2003 Yamada et al.
2002/0156180 A1 10/2002 Yamada et al.

FOREIGN PATENT DOCUMENTS

CN 103396549 11/2013
JP 2003-292795 10/2003

OTHER PUBLICATIONS

Kumar et al., "Synthesis of substituted amines and isoindolinones: catalytic reductive amination using abundantly available AlCl3/PMHS", Green Chemistry, Oct. 2012, pp. 3410-3414, vol. 14, No. 12.
Chandrasekhar et al., "Regioselective Reductive Ring Opening of Cyclic 1,2- and 1,3-Benzylidene Acetals", Chemistry Letters, 1998, pp. 1273-1274, vol. 27, No. 12.
International Search Report, dated May 11, 2016, from corresponding PCT application No. PCT/FR2016/050201.
FR Search Report, dated Sep. 1, 2015, from corresponding FR application No. 1500177.

Primary Examiner — Sikarl A Witherspoon
(74) Attorney, Agent, or Firm — Young & Thompson

(57) ABSTRACT

Disclosed is an adduct between a Lewis acid, preferably aluminum trichloride, iron trichloride, or zinc dichloride, and a hydrosilane;—a method for preparing same; and a method for for reducing, particularly, an aldehyde, a ketone, an α,β-unsaturated ketone, an imine, or an α,β-unsaturated imine.

24 Claims, 1 Drawing Sheet

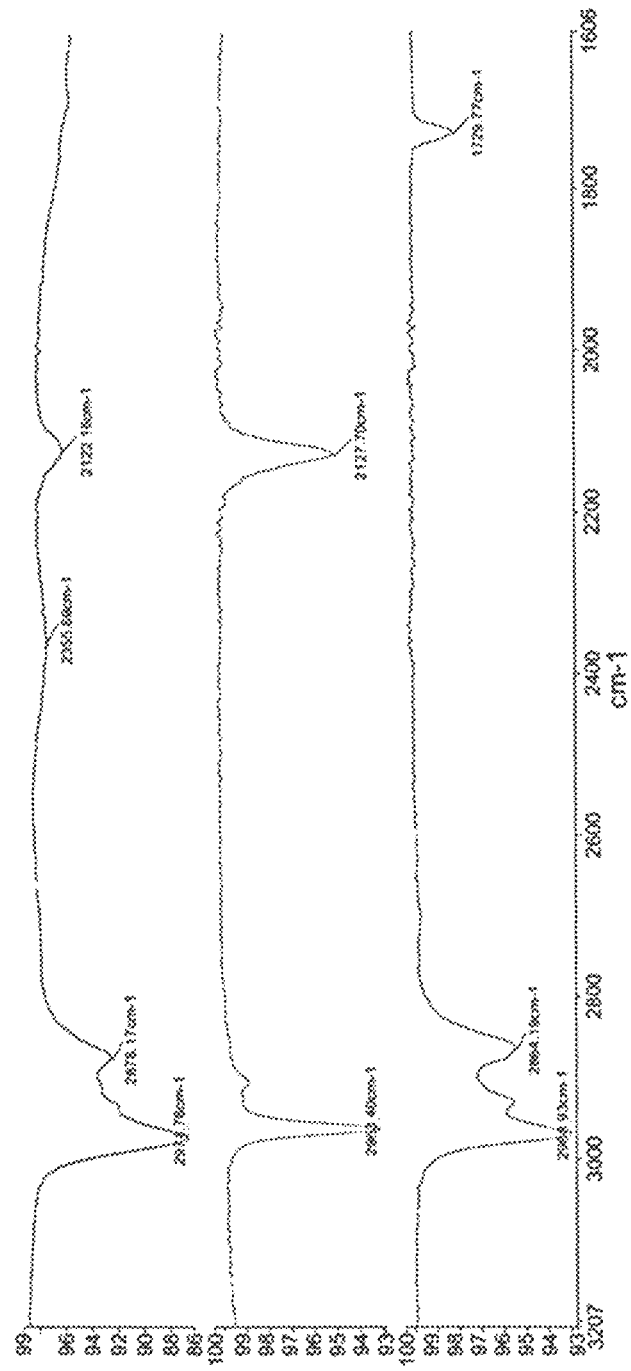

HYDROSILANE/LEWIS ACID ADDUCT, PARTICULARLY ALUMINUM, IRON, AND ZINC, METHOD FOR PREPARING SAME, AND USE OF SAID SAME IN REACTIONS FOR REDUCING CARBONYL DERIVATIVES

The present invention relates to the field of synthesis of alcohols, ketones, and ethers by reduction of a ketone or an enone by an adduct between a Lewis acid, advantageously aluminium trichloride, iron trichloride or zinc dichloride, and a silane hydride donor.

The synthetic chemistry industry is currently undergoing a paradigm shift. The current "all natural", "all organic" craze has created a new market oriented towards "green" products. Meanwhile, the toughening of the REACH regulation and the poor public perception of chemistry are converging towards a new approach within the field of chemistry, which today aspires to be eco-friendly. This rapid evolution is reflected by the development of new environmentally friendly synthesis methods focussed on the preparation of bio-sourced products. This is a real scientific and technical challenge, requiring innovation and integration of new synthesis strategies. The cosmetics industries have been the first to become involved in this approach and have demonstrated clearly their interest in the ecological and bio-inspired organic chemistry processes.

The reduction of carbonyl compounds, such as ketones, aldehydes, esters and the nitrogenous derivatives thereof, such as imines and nitro derivatives, is a basic reaction within the field of organic chemistry.

The reduction of these compounds makes it possible to obtain alcohols or amines.

There are a large number of reagents capable of performing these reactions, especially aluminium hydrides or boron hydrides.

Among the available hydride sources, hydrosilanes have only seldom been used to perform the reduction of carbonyl groups due to their relative inertia with respect to these groups.

The reduction of carbonyl groups requires their concomitant activation by Lewis acid, such as tris(pentafluorophenyl)borane, or the activation of the hydride by a transition metal, such as copper or rhodium.

It is also possible to reduce carbonyl groups by activation of the hydrosilane by a nucleophile, such as a fluoride.

Polymethylhydrosiloxane (PMHS) is a waste product produced by the silicone industry. It is an abundant and inexpensive compound having the property of being a hydride donor and is already used in reactions for the reduction of alkenes in the presence of transition metals or as a hydride donor for the reduction of carbonyl groups in the presence of a Lewis acid.

Hydrosilanes such as triethylsilane $(C_2H_5)_3Si$—H are also used as reducing agents. These species are not intrinsically nucleophilic and only react with strongly positively polarised compounds. Their use thus requires the use of catalysts based on transition metals such as rhodium or Lewis acids capable of producing a sufficiently reactive cationic species.

Definitions:

Within the sense of the present invention, "adduct" means the product of the reaction between an appropriate amount of the Lewis acid and the hydrosilane. The adduct differs from the product formed when the same amounts of Lewis acid and hydrosilane are introduced directly into the reaction medium in which the reaction of the reduction of the carbonyl compound is performed. This difference in structure translates especially into a different reactivity and can be detected by analysis methods such as NMR or infrared spectroscopy. The adduct, in the sense of the present invention, is thus pre-formed, i.e. is prepared before an organic synthesis reaction is performed and can therefore be isolated.

The expression "polar aprotic solvent" is used within the present application in the sense that is conventional for a person skilled in the art. Such solvents for example comprise dimethyl sulfoxide, dimethyl formamide, linear or cyclic ethers, and chlorinated solvents.

Within the sense of the present invention, "carbocyclic aryl" means an aromatic unsaturated, monocyclic or polycyclic ring having 5 to 14 members. From the aryls, mention can be made especially of the phenyl, naphthyl and phenanthrenyl groups.

Within the sense of the present invention, "heterocyclic aryl" means an aromatic unsaturated, monocyclic or polycyclic ring having 5 to 10 members, in which one or more of the CH groups has/have been replaced by one or more heteroatoms. From the heteroaryls, mention can be made especially of the pyridyl, pyrrolidinyl, furyl, pyrimidinyl, thienyl, imidazolyl and pyrrolyl groups.

Within the sense of the present invention, "saturated or unsaturated cycloalkyl having 3 to 7 carbon atoms and optionally comprising one or more heteroatoms selected from nitrogen, sulfur or oxygen atoms" means a saturated monocyclic or polycyclic ring having 3 to 7 members. From the cycloalkyls, mention can be made especially of the morpholinyl, pyrrolidinyl, piperidinyl, tetrahydrofuranyl, tetrahydropyranyl and tetrahydrothiophenyl rings.

Within the sense of the present invention, "aralkyl" means an aromatic unsaturated, monocyclic or polycyclic ring having 5 to 14 members connected to the rest of the molecule by an alkyl chain having 1 to 6 carbon atoms. From the aralkyls, mention can be made especially of the benzyl and phenyl ethyl groups.

Within the sense of the present invention, "linear or branched alkylene having at most 12 carbon atoms" means an alkyl chain having 2 to 12 carbon atoms in which there is at least one double bond. From the alkylenes, mention can be made especially of the ethenyl, propenyl, butenyl and heptenyl groups.

Within the sense of the present invention, "optionally substituted" means the fact that one or more hydrogen atoms present on the alkyl or alkylene chain, or on the aryl or heteroaryl ring can be replaced by an atom or a functional group such as an alkyl group, especially methyl, ethyl, propyl or butyl, amino, hydroxy, alkoxy, especially methoxy, ethoxy, propoxy, a halogen, especially a fluorine atom, or a $CF_3$ group.

The present invention relates to an adduct between a Lewis acid, preferably aluminium trichloride, iron trichloride, or zinc dichloride, and a hydrosilane.

The inventors of the present invention have discovered that an adduct of this type between a Lewis acid and a hydrosilane appears to have an increased reactivity compared to a simple mixture of the Lewis acid and the hydrosilane in the reaction medium used for the reduction of an aldehyde, a ketone, an α,β-unsaturated ketone, an imine, or an α,β-unsaturated imine, advantageously a ketone or an α,β-unsaturated ketone.

This increased reactivity is translated especially into an improved yield and an improved selectivity.

The adduct between aluminium trichloride and a hydrosilane also has, in addition to its improved reactivity, the advantage of being stable in the presence of humidity and air, for example by contrast with aluminium trichloride, which must be handled in strict anhydrous conditions and of which the toxicity is well known.

The hydrosilane can be selected from monomeric, oligomeric or polymeric compounds comprising in their structure at least one Si—H group. Examples of hydrosilanes are the trialkylsilanes, such as triethylsilane ($Et_3SiH$) and tri(iso-propyl)silane, tris(trimethylsilyl)silane, triphenylsilane, the hydrosiloxanes, such as polymethylhydrosiloxanes (PMHS), the polydimethylsiloxanes having a terminal SiH group, such as tetramethyldisiloxane, the methylhydro-dimethylsiloxane copolymer, the methylhydrophenyl-methylsiloxane copolymer, the methylhydrocyanopropylsiloxane copolymer, the methylhydromethyloctylsiloxane copolymer, poly(1,2-dimethylhydrosilazane), the (1-methyl-hydrosilazane)(1,2-dimethylhydrosilazane) copolymer, and methylhydrocyclosiloxane.

Advantageously, the hydrosilane is selected from triethylsilane, the polymethylhydrosiloxanes, and the polydimethylsiloxanes having a terminal Si—H group. The polymethylhydrosiloxanes and the polydimethylsiloxanes having a terminal Si—H group are, especially, PMHS or tetramethyldisiloxane.

The Lewis acid is advantageously selected from the salts of zinc (II), tin (II) or (IV), iron (II) or iron (III), copper (I), palladium (II), titanium (III) or (IV), bismuth (III) or aluminium (III), or a mixture of these Lewis acids, advantageously aluminium (III), or iron (III), or zinc (II).

More advantageously, the Lewis acid is aluminium trichloride, iron trichloride, or zinc dichloride.

The ratio between the Lewis acid and the hydrosilane is dependent on the nature of the compound to be reduced and can be adjusted by a person skilled in the art. The ratio between the Lewis acid, advantageously aluminium trichloride, iron trichloride, or zinc dichloride, and the hydrosilane in the adduct is advantageously from 1:1 to 1:50, advantageously from 1:1 to 1:10, more advantageously from 1:1 to 1:5, and especially is 1:20, 1:10, 1:3 or 1:5.

The adduct as described above can also contain one or more additives likely to improve the reactivity of the Lewis acid. The additive can be selected from a second Lewis acid (different form the first Lewis acid of the adduct), preferably in a ratio of 1:1 relative to the hydrosilane, or from a metal salt, an alcohol, advantageously iso-propanol or tert-butanol, preferably in a ratio of 2:1 relative to the Lewis acid, or from a dihalogen, especially cuprous iodide.

Advantageously, the additive is an alcohol selected from iso-propanol and tert-butanol, preferably in a ratio of 2:1 relative to the Lewis acid.

In a first embodiment, the present invention relates to an adduct between aluminium trichloride and a hydrosilane. The adduct can be, especially, an adduct between aluminium trichloride and PMHS, preferably in a molar ratio of 1:1 or 1:5. The adduct can also be an adduct between aluminium trichloride and triethylsilane, preferably in a molar ratio of 0.3:1.

The aluminium-based adduct can also contain one or more additives likely to modulate the reactivity of the Lewis acid, for example by increasing the selectivity in the reduction reactions. The additive can be selected from a second Lewis acid, advantageously zinc dichloride, preferably in a ratio of 1:1 relative to the hydrosilane, from a metal salt, from an alcohol, advantageously iso-propanol or tert-butanol, preferably in a ratio of 2:1 relative to the aluminium, or from a dihalogen, especially cuprous iodide.

The additive is advantageously an alcohol selected from iso-propanol and tert-butanol, preferably in a ratio of 2:1 relative to the Lewis acid.

In a preferred embodiment, the present invention relates to an adduct as described above between aluminium trichloride, triethylsilane and iso-propanol, preferably in a molar ratio of 0.3:1:0.6.

In a second embodiment, the present invention relates to an adduct between iron trichloride and a hydrosilane. The adduct can be, especially, an adduct between iron trichloride and PMHS or an adduct between iron trichloride and triethylsilane. Advantageously, the molar ratio $FeCl_3$:TES or PMHS can vary from 0.01:1 to 1:1, advantageously from 0.05:1 to 0.3:1. An adduct in which the ratio Fe/TES or PMHS is 0.3:1 or 0.15:1 is preferred.

The iron-based adduct can also contain one or more additives likely to modulate the reactivity of the Lewis acid, for example by increasing the selectivity in the reduction reactions. The additive can be selected from a second Lewis acid, advantageously zinc dichloride, preferably in a ratio of 1:1 relative to the hydrosilane, from a metal salt, from an alcohol, advantageously iso-propanol or tert-butanol, preferably in a ratio of 2:1 relative to the aluminium, or from a dihalogen, especially cuprous iodide.

Advantageously, the additive is an alcohol selected from iso-propanol and tert-butanol, preferably in a ratio of 2:1 relative to the Lewis acid.

In a preferred embodiment, the present invention relates to an adduct between iron trichloride, triethylsilane and an alcohol, especially selected from iso-propanol and tert-butanol. The ratio between the $FeCl_3$ and the alcohol is advantageously 1:2. The present invention thus relates especially to an adduct TES/$FeCl_3$/i-PrOH or t-BuOH in a molar ratio 1:x:2x, where X varies from 0.01 to 1, advantageously from 0.05 to 0.3 and is preferably 0.05.

The adduct defined above is advantageously obtained by a method comprising a step of heating the Lewis acid, preferably aluminium trichloride, and the hydrosilane in a polar aprotic solvent or in the absence of solvent.

The solvent is advantageously anhydrous.

Advantageously, the polar aprotic solvent is selected from linear and cyclic ethers. It is advantageously diethyl ether, tert-butyl ether and methyl ether, tetrahydrofuran, cyclopentyl methyl ether and 2-methyltetrahydrofuran, especially 2-methyltetrahydrofuran or cyclopentyl methyl ether. 2-methyltetrahydrofuran, because it is a solvent obtained from biomass and thus respects the principles of green chemistry, and cyclopently methyl ether, due to its stability and capacity to limit the formation of peroxides, are the preferred solvents.

The reactions can also be carried out advantageously without solvent.

Advantageously, the adduct is advantageously obtained at a temperature from 10 to 120° C., more advantageously from 30 to 100° C., especially from 55 to 80° C. The reaction time is dependent on the temperature and is from 10 minutes to 180 minutes. The reaction time is typically between 10 and 40 minutes at a temperature of 70° C. The reduction of the temperature leads to an increase in this reaction time.

In an especial embodiment, the adduct is obtained in the 2-methyltetrahydrofuran at a temperature of approximately 70° C. over a period of 30 minutes.

The present invention also relates to an adduct between a Lewis acid as obtained by the method described above.

In a first embodiment, the present invention relates to an adduct between aluminium trichloride and a hydrosilane selected from PMHS, triethylsilane and tetramethyldisilane, and optionally an additive, as defined above, obtained by heating to a temperature of from 50 to 80° C. in a polar aprotic solvent, advantageously an ether such as 2-methyltetrahydrofuran, cyclopentyl methyl ether, or without solvent.

In a second embodiment, the present invention also relates to an adduct between iron trichloride and a hydrosilane selected from PMHS, triethylsilane and tetramethyldisilane, and optionally an additive, as defined above, obtained by heating to a temperature of from 50 to 80° C. in a polar aprotic solvent, advantageously an ether such as 2-methyltetrahydrofuran, cyclopentyl methyl ether, or without solvent.

The present invention also relates to the use of an adduct between a Lewis acid, preferably aluminium trichloride or iron trichloride, a hydrosilane and optionally an additive, as defined above, in a reduction reaction, especially the reduction of an aldehyde, a ketone, an α,β-unsaturated ketone, an imine, or an α,β-unsaturated imine, advantageously a ketone or an α,β-unsaturated ketone.

Advantageously, the amount of adduct is selected so as to comprise 1 to 5 hydride equivalents per mole of aldehyde, α,β-unsaturated aldehyde, ketone, α,β-unsaturated ketone, imine, or α,β-unsaturated imine, advantageously ketone or α,β-unsaturated ketone.

The amount of adduct is advantageously selected so as to comprise 1 to 1.5 hydride equivalents per mole of α,β-unsaturated aldehyde, α,β-unsaturated ketone, or α,β-unsaturated imine, advantageously α,β-unsaturated ketone, or 4 to 5 hydride equivalents per mole of aldehyde, ketone or imine, advantageously ketone.

The number of hydride equivalents can be easily calculated by a person skilled in the art. If the hydrosilane is a monomeric compound such as triethylsilane, the number of hydride equivalents corresponds to the equivalent number of the monomeric hydrosilane. For example, in the case of triethylsilane, 1 mole of hydride will correspond to 1 mole of triethylsilane present in the adduct. If the hydrosilane is an oligomeric or polymeric silane such as PMHS, the number of hydrides is calculated on the basis of the hydride content of the polymer, determined by assay. This content is also provided in the case of commercial products. For example, PMHS is sold in a form containing 1 mmol of hydride per volume of 60 μL of PMHS.

Of course, the amount of adduct can be determined by a person skilled in the art depending on the substrate and the desired product. For example, in order to obtain an alcohol from an α,β-unsaturated ketone, at least two hydride equivalents per mole of α,β-unsaturated ketone are necessary.

The reduction is performed at a temperature of from 0 to 100° C., advantageously from 15 to 80° C.

The reduction is performed in a polar aprotic solvent, advantageously a linear or cyclic ether, especially diethyl ether, tert-butyl ether and methyl ether, tetrahydrofuran, cyclopentyl methyl ether and 2-methyltetrahydrofuran, preferably 2-methyltetrahydrofuran or cyclopentyl methyl ether, or in the absence of solvent. The solvent can also be an ester, for example an ester of acetic acid, such as ethyl acetate or butyl acetate.

The adduct can be used alone or in combination with another Lewis acid, with a metal salt, with a dihalogen, or with an alcohol.

The inventors have demonstrated an improvement of the selectivity of reduction reactions in which the adduct between aluminium trichloride or iron trichloride and a hydrosilane is used when an additive such as another Lewis acid, a metal salt, a dihalogen or an alcohol is introduced into the reaction medium or when an adduct between aluminium trichloride or iron trichloride, a hydrosilane and an additive is used. In the case of the reduction of an α,β-unsaturated ketone, this improvement is translated into a total selectivity for the saturated ketone resulting from the 1,4 reduction of said α,β-unsaturated ketone.

Advantageously, the other Lewis acid is titanium trichloride or zinc dichloride, the metal salt comprises at least one iodide ion, advantageously cuprous iodide, the dihalogen is iodine $I_2$, or the alcohol is iso-propanol or tert-butanol.

In one embodiment, the adduct between aluminium trichloride or iron trichloride and hydrosilane is used in combination with iodine, cuprous iodide, zinc dichloride, iso-propanol or tert-butanol. An adduct between iron trichloride or aluminium trichloride, hydrosilane and iso-propanol or tert-butanol is advantageously used.

If another Lewis acid, a metal salt, a dihalogen or an alcohol is used with the adduct, the ratio between the hydrosilane and the other Lewis acid, the metal salt or the dihalogen varies from 1:3 to 1:1, and especially is 1:1.2.

If the compound to be reduced is an α,β-unsaturated ketone, an α,β-unsaturated imine or an α,β-unsaturated aldehyde, advantageously an α,β-unsaturated ketone, the adduct is advantageously an adduct between a Lewis acid, advantageously aluminium trichloride or iron trichloride, and a trialkylsilane, advantageously triethylsilane. The adduct is especially advantageously an adduct prepared with another Lewis acid, advantageously zinc dichloride, preferably in a ratio of 1:1 relative to the hydrosilane, a metal salt, an alcohol, advantageously iso-propanol or tert-butanol, preferably in a ratio of 2:1 relative to the aluminium trichloride or iron trichloride, or a dihalogen, especially cuprous iodide or iodine.

If the compound to be reduced is a ketone, an imine or a saturated aldehyde, advantageously a ketone, the adduct is advantageously an adduct between a Lewis acid, advantageously aluminium trichloride, iron trichloride or zinc dichloride, and a hydrosilane, advantageously PMHS, TMDS or triethylsilane, preferably triethylsilane.

The inventors have been able to demonstrate that the choice of the adduct makes it possible to control the product obtained by the reaction. In the case of saturated ketones in which the carbons adjacent to the carbonyl group C=O are $CH_2$ groups, the use of an adduct between a Lewis acid, advantageously aluminium trichloride or iron trichloride, and PMHS or triethylsilane makes it possible to obtain selectively an ether, and the use of an adduct between zinc dichloride and triethylsilane makes it possible to obtain selectively an alcohol.

The selectivity of the reaction, and therefore the product obtained, are dependent on the adduct used and the solvent. For example, in the case of cyclohexanone, the adducts [PMHS-AlCl₃], [TMDS-AlCl₃], [TES-AlCl₃], preferably [TES-AlCl₃], promote the formation of ether in 2-methyltetrahydrofuran. Adducts such as [TES-ZnCl₂] make it possible to control the reduction to the corresponding alcohol in cyclopentyl methyl ether.

The present invention advantageously relates to the use as described above of an adduct between a Lewis acid, advantageously aluminium trichloride, iron trichloride or zinc dichloride, and a hydrosilane for the reduction of a compound comprising a cyclopentanone, cyclopentenone, cyclohexanone or cyclohexenone motif or an aryl-vinyl ketone motif. These compounds are commonly used in the cosmetics industry due to their fragrant and/or aromatic properties, especially in the preparation of perfumes. Mention can be made by way of example of jasmone and dihydrojasmone for the cyclopentanones and cyclopentenones, pulegone and menthone for the cyclohexenones and cyclohexanones, or frambinone for the aryl-vinyl ketones. Other compounds having these types of structures and having fragrant and/or aromatic properties and/or having such a structure known to a person skilled in the art can be reduced by the method described above and below.

Advantageously, the compound to be reduced is a linear ketone, α,β-unsaturated ketone, imine or α,β-unsaturated imine of formula (Ia):

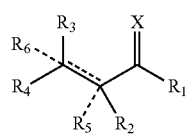
(Ia)

in which:

X is O or $NR_a$, $R_a$ being selected from linear or branched alkyl having at most 12 carbon atoms, linear or branched alkylene having at most 6 carbon atoms, carbocyclic or heterocyclic aryl, an aralkyl radical, each of these alkyl, alkylene, aralkyl or aryl radicals being optionally substituted, ═══ is a single bond or a double bond, $R_1$ is a linear or branched alkyl radical having at most 12 carbon atoms, linear or branched alkylene having at most 12 carbon atoms, a saturated or unsaturated cycloalkyl radical having 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aryl, aralkyl or cycloalkyl radicals being optionally substituted, $R_2$ is hydrogen, linear or branched alkyl having at most 12 carbon atoms, linear or branched alkylene having at most 6 carbon atoms, carbocyclic or heterocyclic aryl, each of these alkyl, alkylene or aryl radicals being optionally substituted, $R_3$ and $R_4$, which are identical or different, are hydrogen, linear or branched alkyl having at most 12 carbon atoms, linear or branched alkylene having at most 6 carbon atoms, carbocyclic or heterocyclic aryl, an aralkyl radical, each of these alkyl, alkylene, aralkyl or aryl radicals being optionally substituted, and when ═══ is a single bond, $R_5$ is hydrogen, linear or branched alkyl having at most 12 carbon atoms, linear or branched alkylene having at most 12 carbon atoms, carbocyclic or heterocyclic aryl, an aralkyl radical, each of these alkyl, alkylene, aralkyl or aryl radicals being optionally substituted, and $R_6$ is hydrogen, linear or branched alkyl having at most 12 carbon atoms, linear or branched alkylene having at most 12 carbon atoms, carbocyclic or heterocyclic aryl, an aralkyl radical, each of these alkyl, alkylene, aralkyl or aryl radicals being optionally substituted, or a cyclic ketone, α,β-unsaturated ketone, imine or α,β-unsaturated imine of formula (Ib):

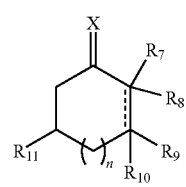
(Ib)

in which:

n=0 or 1,

X and ═══ are as defined above, $R_7$ is a linear or branched alkyl radical having at most 12 carbon atoms, linear or branched alkylene having at most 12 carbon atoms, a saturated or unsaturated cycloalkyl radical having 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl, aryl or cycloalkyl radicals being optionally substituted, advantageously an alkyl radical having at most 12 carbon atoms, $R_9$ a hydrogen, a linear or branched alkyl having at most 12 carbon atoms, linear or branched alkylene having at most 12 carbon atoms, a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl or aryl radicals being optionally substituted, or a $CHR_{12}$—$COOR_{13}$ group, in which $R_{12}$ is hydrogen, a linear or branched alkyl radical having at most 12 carbon atoms, and $R_{13}$ is a linear or branched alkyl radical having at most 12 carbon atoms, a saturated or unsaturated cycloalkyl radical having from 3 to 7 carbon atoms and optionally comprising one or more heteroatoms selected from nitrogen, sulfur or oxygen atoms, a carbocyclic aryl radical, an aralkyl radical, each of these alkyl, alkylene, aralkyl or aryl radicals being optionally substituted, and when ═══ is a single bond, $R_8$ and $R_{10}$, which are identical or different, are a hydrogen, a linear or branched alkyl radical having at most 12 carbon atoms, linear or branched alkylene having at most 12 carbon atoms, a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl or aryl radicals being optionally substituted, or a $CHR_{12}$—$COOR_{13}$ group, in which $R_{12}$ is hydrogen, a linear or branched alkyl radical having at most 12 carbon atoms, and $R_{13}$ is a linear or branched alkyl radical having at most 12 carbon atoms, a saturated or unsaturated cycloalkyl radical having from 3 to 7 carbon atoms and optionally comprising one or more heteroatoms selected from nitrogen, sulfur or oxygen atoms, or a carbocyclic aryl radical, $R_{11}$ is a hydrogen, a linear or branched alkyl radical having at most 12 carbon atoms, linear or branched alkylene having at most 12 carbon atoms, a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl or aryl radicals being optionally substituted, advantageously an alkyl radical having at most 12 carbon atoms, or, when ═══ is a single bond, $R_7$ and $R_8$ are together a ═CH—$R_{7a}$ group where $R_{7a}$ is hydrogen, a linear or branched alkyl radical having at most 11 carbon atoms, a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl or aryl radicals being optionally substituted, advantageously an alkyl radical having at most 11 carbon atoms.

Thus, in compounds of formula (Ia) and (Ib) in which ≕ is a double bond, the groups $R_5$ and $R_6$ are absent from the compound of formula (Ia) and the groups $R_8$ and $R_{10}$ are absent from the compound of formula (Ib).

The compound to be reduced is especially an α,β-unsaturated ketone or an α,β-unsaturated imine, advantageously an α,β-unsaturated ketone, of the following formula (Ia1):

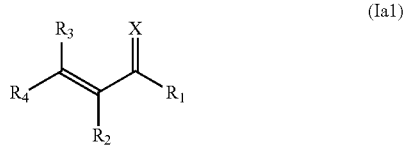

(Ia1)

in which X, $R_1$, $R_2$, $R_3$ and $R_4$ are as defined above, or a cyclic α,β-unsaturated ketone of formula (Ib1):

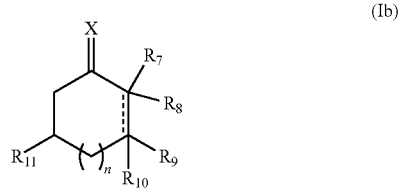

(Ib)

in which:
n=0 or 1,
X, $R_7$, $R_8$, $R_9$, $R_{10}$ and $R_{11}$ are as defined above,
≕ is a double bond.

When the compound is a compound of formula (Ia1) or (Ib1), the adduct can be advantageously an adduct between aluminium trichloride, a hydrosilane, selected especially from triethylsilane and PMHS, preferably triethylsilane, and an alcohol selected from iso-propanol and tert-butanol, advantageously in a ratio of 0.3:1:0.6. The reduction of the α,β-unsaturated ketone with an adduct between aluminium trichloride and a hydrosilane can also be performed in the presence of another Lewis acid, preferably zinc dichloride, advantageously in a ratio of 1:1 relative to the aluminium and in the absence of solvent. The adduct can also be advantageously an adduct between iron trichloride, a hydrosilane, especially selected from triethylsilane and PMHS, preferably triethylsilane, and an alcohol selected from iso-propanol and tert-butanol, advantageously in a ratio of x:1:2x, where X varies from 0.01 to 1, advantageously from 0.05 to 0.3 and is preferably 0.05.

In an advantageous embodiment, the present invention relates to the use of an adduct as described above for the reduction of a linear α,β-unsaturated ketone (X=O) of formula (Ia1) in which $R_2$ is hydrogen or a linear or branched alkyl radical having at most 12 carbon atoms, advantageously hydrogen, and one of the substituents $R_3$ or $R_4$ is hydrogen, a linear or branched alkyl radical having at most 12 carbon atoms, and the other substituent is an optionally substituted carbocyclic aryl radical.

The present invention relates more especially to the use of an adduct between a Lewis acid, advantageously aluminium trichloride, iron trichloride or zinc dichloride, and a hydrosilane for the reduction of a compound of the following formula (IIa):

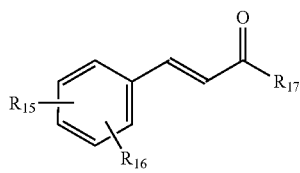

in which:
$R_{15}$ and $R_{16}$ are, independently of one another, hydrogen, an optionally substituted linear or branched alkyl radical having at most 12 carbon atoms, advantageously selected from methyl, ethyl, propyl, advantageously isopropyl, and butyl, advantageously tert-butyl, an optionally substituted linear or branched alkylene radical having at most 12 carbon atoms, an optionally substituted linear or branched alkoxy radical having at most 12 carbon atoms, advantageously selected from methoxy, ethoxy, propoxy, advantageously isopropoxy, and butoxy, advantageously tert-butoxy, OH, $COOR_{13}$ where $R_{13}$ is as defined above, $CF_3$, halogen selected from F, Cl, Br and I, said substituents $R_{15}$ and $R_{16}$ being positioned in the ortho, meta or para position of the ring, advantageously in the meta and para positions, $R_{15}$ and $R_{16}$ advantageously being selected from an optionally substituted linear or branched alkoxy radical having at most 12 carbon atoms, especially methoxy, ethoxy, propoxy, advantageously isopropoxy, and butoxy, advantageously tert-butoxy, an optionally substituted linear or branched alkyl radical having at most 12 carbon atoms, advantageously selected from methyl, ethyl, propyl, advantageously isopropyl, and butyl, advantageously tert-butyl, and OH, and $R_{17}$ is a linear or branched alkyl radical having at most 12 carbon atoms, linear or branched alkylene having at most 12 carbon atoms, a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of these alkyl, alkylene, aralkyl or aryl radicals being optionally substituted, advantageously an alkyl group selected from methyl, ethyl, propyl, advantageously isopropyl, and butyl, advantageously tert-butyl, especially methyl.

Advantageously, the compound of formula (IIa) is a ketone of the following formula (IIa1):

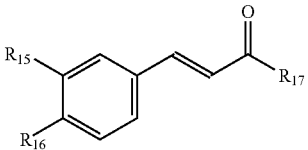

in which:
$R_{15}$ and $R_{16}$ are, independently of one another, hydrogen, an optionally substituted linear or branched alkoxy radical having at most 12 carbon atoms, especially methoxy, ethoxy, propoxy, advantageously isopropoxy, and butoxy, advantageously tert-butoxy, methyl, ethyl, propyl, advantageously isopropyl, and butyl, advantageously tert-butyl, and OH, $R_{17}$ is a radical selected from methyl, ethyl and butyl, especially methyl.

The present invention also relates to a method for preparing a compound of the following formula (IIIb):

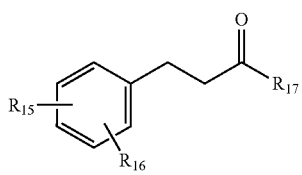

in which:

$R_{15}$ and $R_{16}$ are, independently of one another, hydrogen, an optionally substituted linear or branched alkyl radical having at most 12 carbon atoms, advantageously selected from methyl, ethyl, isopropyl, and tert-butyl, an optionally substituted linear or branched alkylene radical having at most 12 carbon atoms, an optionally substituted linear or branched alkoxy radical having at most 12 carbon atoms, advantageously selected from methoxy, ethoxy, propoxy, advantageously isopropoxy, and butoxy, advantageously tert-butoxy, OH, COOR$_{13}$ where $R_{13}$ is as defined above, CF$_3$, halogen selected from F, Cl, Br and I, said substituents $R_{15}$ and $R_{16}$ being positioned in the ortho, meta or para position of the ring, advantageously in the meta and para positions, $R_{15}$ and $R_{16}$ advantageously being selected from an optionally substituted linear or branched alkoxy radical having at most 12 carbon atoms, especially methoxy, ethoxy, propoxy, advantageously isopropoxy, and butoxy, advantageously tert-butoxy, and OH, $R_{17}$ is a linear or branched alkyl radical having at most 12 carbon atoms, advantageously an alkyl group selected from methyl, ethyl, propyl, advantageously isopropyl, and butyl, advantageously tert-butyl, especially methyl, comprising a step of contacting a compound of formula (IIa)

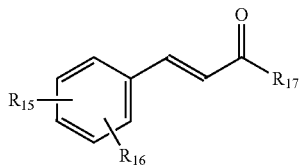

with an adduct between a Lewis acid, advantageously aluminium trichloride, iron trichloride or zinc dichloride, and a hydrosilane as defined above.

Advantageously, the compound of formula (IIa) is contacted with an adduct between a Lewis acid, advantageously aluminium trichloride, iron trichloride or zinc dichloride, and a hydrosilane in the presence of an iodised derivative, such as iodine or cuprous iodide, or in the presence of an alcohol, such as iso-propanol or tert-butanol.

Advantageously, the adduct is an adduct between aluminium trichloride or iron trichloride and a hydrosilane selected from PMHS, triethylsilane and tetramethyldisilane, especially triethylsilane as defined above in the presence of an iodised derivative, such as iodine or cuprous iodide, or in the presence of an alcohol, such as iso-propanol or tert-butanol, or in the presence of a Lewis acid, especially zinc dichloride.

More advantageously, the adduct between aluminium trichloride or iron trichloride and a hydrosilane is used in the presence of tert-butanol or iso-propanol or zinc dichloride.

The method is preferably carried out in a polar aprotic solvent as defined above, preferably methyltetrahydrofuran.

The present invention also relates to a method for preparing a compound of the following formula (IIIa1):

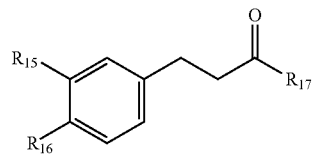

in which:

$R_{15}$ and $R_{16}$ are, independently of one another, hydrogen, an optionally substituted linear or branched alkyl radical having at most 12 carbon atoms, advantageously selected from methyl, ethyl, isopropyl, and tert-butyl, an optionally substituted linear or branched alkylene radical having at most 12 carbon atoms, an optionally substituted linear or branched alkoxy radical having at most 12 carbon atoms, advantageously selected from methoxy, ethoxy, propoxy, advantageously isopropoxy, or butoxy, advantageously tert-butoxy, OH, COOR$_{13}$ where $R_{13}$ is as defined above, CF$_3$, halogen selected from F, Cl, Br and I, said substituents $R_{15}$ and $R_{16}$ being positioned in the ortho, meta or para position of the ring, advantageously in the meta and para positions, $R_{15}$ and $R_{16}$ being selected advantageously from an optionally substituted linear or branched alkoxy radical having at most 12 carbon atoms, especially methoxy, ethoxy, propoxy, advantageously isopropoxy, and butoxy, advantageously tert-butoxy, and OH, $R_{17}$ is a linear or branched alkyl radical having at most 12 carbon atoms, advantageously selected from methyl, ethyl, propyl, advantageously isopropyl, and butyl, advantageously tert-butyl, comprising a step of contacting a compound of formula (IIa1)

![](cinnamate structure)

with an adduct between a Lewis acid, advantageously aluminium trichloride, iron trichloride or zinc dichloride, and a hydrosilane.

In an especial embodiment, the compound of formula (IIa1) is a ketone of the following formula (IIa1a):

![](cinnamate structure with R15, R16, R17)

in which:

$R_{15}$ is an optionally substituted linear or branched alkoxy radical having at most 12 carbon atoms, especially methoxy, ethoxy, propoxy, advantageously isopropoxy, and butoxy, advantageously tert-butoxy;

$R_{16}$ is OH, $R_{17}$ is a radical selected from methyl, ethyl and butyl.

The compound of formula IIa1a is selected especially from those in which $R_{15}$ is methoxy, $R_{16}$ is OH and $R_{17}$ is methyl; $R_{15}$ is ethoxy, $R_{16}$ is OH and $R_{17}$ is methyl; $R_{15}$ is n-propoxy, $R_{16}$ is OH and $R_{17}$ is methyl; $R_{15}$ is i-propoxy, $R_{16}$ is OH and $R_{17}$ is methyl; $R_{15}$ is n-butoxy, $R_{16}$ is OH and $R_{17}$ is methyl; $R_{15}$ is i-butoxy, $R_{16}$ is OH and $R_{17}$ is methyl; and $R_{15}$ is t-butoxy, $R_{16}$ is OH and $R_{17}$ is methyl; $R_{15}$ is methoxy, $R_{16}$ is OH and $R_{17}$ is ethyl; $R_{15}$ is ethoxy, $R_{16}$ is OH and $R_{17}$ is ethyl; $R_{15}$ is n-propoxy, $R_{16}$ is OH and $R_{17}$ is ethyl; $R_{15}$ is i-propoxy, $R_{16}$ is OH and $R_{17}$ is ethyl; $R_{15}$ is n-butoxy, $R_{16}$ is OH and $R_{17}$ is ethyl; $R_{15}$ is i-butoxy, $R_{16}$ is OH and $R_{17}$ is ethyl; and $R_{15}$ is t-butoxy, $R_{16}$ is OH and $R_{17}$ is ethyl; $R_{15}$ is methoxy, $R_{16}$ is OH and $R_{17}$ is propyl; $R_{15}$ is ethoxy, $R_{16}$ is OH and $R_{17}$ is propyl; $R_{15}$ is n-propoxy, $R_{16}$ is OH and $R_{17}$ is propyl; $R_{15}$ is i-propoxy, $R_{16}$ is OH and $R_{17}$ is propyl; $R_{15}$ is n-butoxy, $R_{16}$ is OH and $R_{17}$ is propyl; $R_{15}$ is i-butoxy, $R_{16}$ is OH and $R_{17}$ is propyl; and $R_{15}$ is t-butoxy, $R_{16}$ is OH and $R_{17}$ is propyl; $R_{15}$ is methoxy, $R_{16}$ is OH and $R_{17}$ is butyl; $R_{15}$ is ethoxy, $R_{16}$ is OH and $R_{17}$ is butyl; $R_{15}$ is n-propoxy, $R_{16}$ is OH and $R_{17}$ is butyl; $R_{15}$ is i-propoxy, $R_{16}$ is OH and $R_{17}$ is butyl; $R_{15}$ is n-butoxy, $R_{16}$ is OH and $R_{17}$ is butyl; $R_{15}$ is i-butoxy, $R_{16}$ is OH and $R_{17}$ is butyl; and $R_{15}$ is t-butoxy, $R_{16}$ is OH and $R_{17}$ is butyl.

When the compound is of formula (Ia1), (IIa), (IIa1) or (IIa1a) above, advantageously a ketone, the adducts between a Lewis acid, advantageously aluminium trichloride or iron trichloride or zinc dichloride, and a hydrosilane selected from the trialkylsilanes, such as triethylsilane ($Et_3SiH$) and tri(isopropyl)silane, tris(trimethylsilyl)silane, triphenylsilane, and the hydrosiloxanes, such as the polymethylhydrosiloxanes (PMHS) and tetramethyldisiloxane, are used. More advantageously, the ketone is reduced with an adduct comprising another Lewis acid, a metal salt, a dihalogen or an alcohol, especially cuprous iodide, iodine, iso-propanol or tert-butanol. In the case of α,β-unsaturated ketones which are not very reactive, such as those of formula (IIa1) or (IIa1a), the alcohol is preferably iso-propanol.

When the adduct is an adduct of $FeCl_3$, the reduction is advantageously carried out in an ester of acetic acid as solvent, for example ethyl acetate or butyl acetate. The reduction is even more advantageously carried out at a substrate concentration varying from 1 M to 5 M, especially from 2 to 4 M. The temperature at which the reduction is performed is dependent on the substrate and can be easily determined by a person skilled in the art. The temperature is typically from 20 to 100° C., especially from 30 to 80° C.

Advantageously, the invention relates to the use of an adduct as described above for the reduction of a cyclic ketone or imine, advantageously a ketone, of the following formula (Ib1):

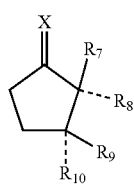
(Ib1)

in which X, $R_7$, $R_8$, $R_9$ and $R_{10}$ are as defined above, or of formula (Ib2):

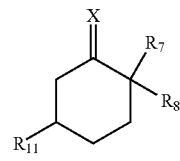

in which X, $R_7$, $R_8$ and $R_{11}$ are as defined above.

From the compounds of formula (Ib2), mention can be made especially of pulegone, in which $R_7$ and $R_8$ together represent a $=CHR_{7a}$ group, where $R_{7a}$ is hydrogen, the reduction of which makes it possible to obtain menthone and/or menthol, which are largely used in the agri-food industry.

The present invention therefore relates, in an especial embodiment, to the use of an adduct between aluminium trichloride or iron trichloride, a hydrosilane selected from triethylsilane and PMHS, and an alcohol selected from iso-propanol and tert-butanol, advantageously in a ratio of 0.3:1:0.6 for the reduction of pulegone into menthone and/or menthol, advantageously into menthol. The reduction of pulegone is preferably performed in the presence of zinc dichloride in a ratio of 1:1 relative to the aluminium trichloride in the absence of solvent.

In an advantageous embodiment, the present invention relates to the use of an adduct as described above for the reduction of a cyclic ketone (X=O) of formula (Ib1) in which:
one of the substituents $R_7$ or $R_8$ is a hydrogen and the other substituent is a linear or branched alkyl radical having at most 12 carbon atoms, linear or branched alkylene having at most 12 carbon atoms, especially a linear alkyl radical having at most 12 carbon atoms,
one of the substituents $R_9$ or $R_{10}$ is hydrogen and the other substituent is a linear or branched alkyl radical having at most 12 carbon atoms or a $CHR_{12}$—$COOR_{13}$ group as defined above, advantageously in which $R_{12}$ is hydrogen and $R_{13}$ is a linear or branched alkyl radical having at most 12 carbon atoms, especially a methyl, ethyl, propyl or butyl radical.

The present invention relates more especially to the use of an adduct between a Lewis acid, advantageously aluminium trichloride, iron trichloride or zinc dichloride, and a hydrosilane for the reduction of a compound of the following formula (IIb):

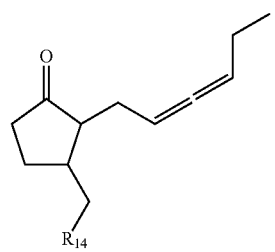

in which:
=== is a single bond or a double bond,
$R_{14}$ is a linear or branched alkyl radical having at most 11 carbon atoms, a linear or branched alkylene having at most 11 carbon atoms, especially a linear alkyl radical having at most 11 carbon atoms or a $COOR_{13}$ group as defined above, advantageously in which $R_{13}$ is a linear or branched alkyl radical having at most 12 carbon atoms, especially a methyl, ethyl, propyl or butyl radical.

The present invention also relates to a method for preparing a compound of the following formula (IIIb):

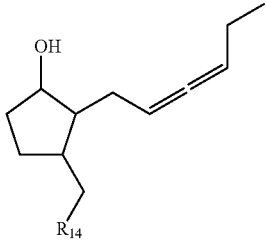

in which:
$=\!=$ is a single bond or a double bond,
$R_{14}$ is hydrogen, a linear or branched alkyl radical having at most 11 carbon atoms, a linear or branched alkylene having at most 11 carbon atoms, especially a linear alkyl radical having at most 11 carbon atoms or a $COOR_{13}$ group as defined above, advantageously in which $R_{13}$ is a linear or branched alkyl radical having at most 12 carbon atoms, especially a methyl, ethyl, propyl or butyl radical, comprising a step of contacting a compound of formula (IIb)

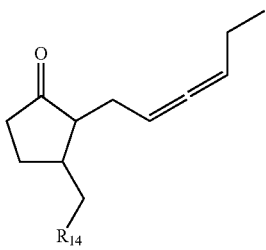

with an adduct between a Lewis acid, advantageously aluminium trichloride, iron trichloride or zinc dichloride, and a hydrosilane as defined above.

When the compound is of formula (Ib1), (Ib2) or (IIb) above, advantageously a ketone, an adduct between a Lewis acid, advantageously aluminium trichloride, iron trichloride or zinc dichloride, and a hydrosiloxane, especially a polymethylhydrosiloxane (PMHS) or tetramethyldisiloxane, is preferably used.

The reduction of compounds of formula (Ib1), (Ib2) or (IIb) is preferably carried out with an adduct $AlCl_3$/TES/i-PrOH in a molar ratio of 0.3:1:0.6; $FeCl_3$/TES/iPrOH in a molar ratio of x:2:2x; or $FeCl_3$/TES/t-BuOH in a molar ratio of x:2:2x, where X varies from 0.01 to 1, advantageously from 0.05 to 0.3 and is preferably 0.05. For the reduction of these compounds with an adduct of $FeCl_3$, 2 equivalents of triethylsilane are thus preferably used. When the adduct is an adduct of $FeCl_3$, the reduction is advantageously carried out in an ester of acetic acid as solvent, for example ethyl acetate or butyl acetate.

The inventors have demonstrated that if the substrate to be reduced is unhindered, the high reactivity of the adducts can be utilised to form ethers.

The present invention also relates to the use of an adduct between a Lewis acid, advantageously aluminium trichloride or iron trichloride, preferably aluminium trichloride, and a hydrosilane, advantageously a hydrosilane such as PMHS or triethylsilane, for the reduction of a compound of the following formula (IV):

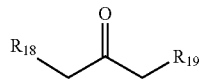

in which $R_{18}$ and $R_{19}$ are, independently of one another, an optionally substituted linear or branched alkyl radical having at most 11 carbon atoms, or $R_{18}$ and $R_{19}$ are linked together to form a saturated or unsaturated cycloalkyl radical having from 3 to 7 carbon atoms and optionally comprising one or more heteroatoms selected from nitrogen, sulfur or oxygen atoms:

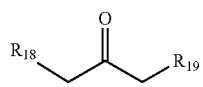

Advantageously, the present invention relates to the use of an adduct between a Lewis acid, advantageously aluminium trichloride or iron trichloride, preferably aluminium trichloride, and a hydrosilane for the reduction of a cyclic ketone of the following formula (IVa):

in which n=1 to 4, advantageously 2 or 3, and optionally comprising one or more heteroatoms selected from nitrogen, sulfur or oxygen atoms,
into a dicycloalkylether of the following formula (Va):

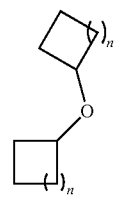

Advantageously, the reduction of the compound of formula (IVa) or (Va) is advantageously performed with an adduct between aluminium trichloride and a hydrosilane, especially PMHS or triethylsilane, preferably in methyl-THF.

The use of an adduct between aluminium trichloride and a hydrosilane, advantageously PMHS or triethylsilane, for the reduction of a ketone in the presence of an alcohol enables the formation of a mixed ether between said ketone and said alcohol.

The present invention thus also relates to the use of an adduct between a Lewis acid, advantageously aluminium trichloride or iron trichloride, preferably aluminium trichloride, and a hydrosilane, advantageously PMHS or triethylsilane, for the preparation of a compound formula (Vb):

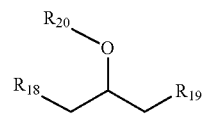

in which $R_{18}$ and $R_{19}$ are, independently of one another, an optionally substituted linear or branched alkyl radical having at most 11 carbon atoms, or $R_{18}$ and $R_{19}$ are linked together to form a saturated or unsaturated cycloalkyl radical having from 3 to 7 carbon atoms and optionally comprising one or more heteroatoms selected from nitrogen, sulfur or oxygen atoms, and $R_{20}$ is a linear or branched alkyl radical having at most 11 carbon atoms, advantageously 1 to 3 carbon atoms.

Preferably, the adduct is an adduct between aluminium trichloride and triethylsilane, advantageously in a ratio of 0.3:1.

Advantageously, the reaction is performed in methyltetrahydrofuran.

In an especial embodiment, the present invention relates to the use of an adduct between aluminium trichloride and triethylsilane, advantageously in a ratio of 0.3:1 for the preparation of cyclopentyl methyl ether or of cyclopentyl ethyl ether.

The present invention also relates to a method for preparing an ether of formula (Vb):

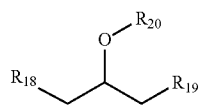

in which $R_{18}$ and $R_{19}$ are, independently of one another, an optionally substituted linear or branched alkyl radical having at most 11 carbon atoms, or $R_{18}$ and $R_{19}$ are linked together to form a saturated or unsaturated cycloalkyl radical having from 3 to 7 carbon atoms and optionally comprising one or more heteroatoms selected from nitrogen, sulfur or oxygen atoms, and $R_{20}$ is a linear or branched alkyl radical having at most 11 carbon atoms, advantageously 1 to 3 carbon atoms.

comprising a step of contacting a ketone of the following formula (IV):

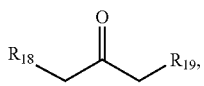

with an alcohol of formula $R_{20}$—OH and an adduct between aluminium trichloride and a hydrosilane, advantageously triethylsilane.

Advantageously, the ketone is a cyclic ketone of the following formula (IVa):

in which n=1 to 4, advantageously 2 or 3, and optionally comprising one or more heteroatoms selected from nitrogen, sulfur or oxygen atoms.

In an advantageous way, the adduct is an adduct between aluminium trichloride and a hydrosilane selected from PMHS and triethylsilane.

Advantageously, the solvent is 2-methyltetrahydrofuran or the contacting step is performed in the absence of solvent.

In an especial embodiment, the present invention relates to a method for preparing cyclopentyl methyl ether comprising a step of contacting cyclopentanone, methanol and an adduct between aluminium trichloride and a hydrosilane, advantageously triethylsilane, preferably in methyltetrahydrofuran or in the absence of solvent.

In an especial embodiment, the present invention relates to a method for preparing cyclopentyl ethyl ether comprising a step of contacting cyclopentanone, ethanol and an adduct between aluminium trichloride and triethylsilane, preferably in methyltetrahydrofuran or in the absence of solvent.

DESCRIPTION OF THE DRAWINGS

FIG. 1 shows the infrared spectrum of an adduct between aluminium trichloride and tetramethyldisilane (top curve) in comparison with that of methyl-THF (bottom curve) and of tetramethyldisilane (middle curve). In the spectrum of the adduct, the intensity of the peaks of the tetramethyldisilane is reduced and some peaks have appeared in different locations, indicating the presence of a new species in the adduct between aluminium trichloride and tetramethyldisilane

EXAMPLES

Example 1

Preparation of the Adduct PMHS-AlCl₃

133 mg (1 mmol) of anhydrous $AlCl_3$, then 500 µL of Me-THF are introduced into a flask equipped with a magnetic stirrer. The mixture is stirred at 25° C. for 10 minutes. Moderate heating is observed due to the dissolution of $AlCl_3$ in the Me-THF. A clear pale pink to red solution is obtained. 300 µL (volume equivalent to 5 mmol hydride) of PMHS are then introduced under stirring at 25° C. A cloudy solution is obtained, this being formed of two immiscible phases. Heating to 70° C. for 30 minutes causes the solution to clear, which then becomes colourless, clear and perfectly homogeneous. The adduct PMHS-AlCl₃ is ready to use in this form. It is stored in a closed container with no need for an inert atmosphere.

Other hydrosilanes can be used instead of PMHS.

For example, tetramethyldisiloxane (TMDS) was also used to prepare an adduct TMDS-AlCl₃ which is just as reactive as the adduct PMHS-AlCl₃ without the need for an excess of hydrosiloxane during the preparation of said adduct.

Example 2

Preparation of the Adducts

Example 2.1

Preparation of the Adduct triethylsilane-AlCl₃

133 mg (1 mmol) of anhydrous $AlCl_3$ are added to 250 ml of Me-THF. Once the $AlCl_3$ has dissolved, 800 µl (5 mmol) of triethylsilane are added. A cloudy solution is obtained having two immiscible phases. After 2 hours of heating to 80° C., a clear and homogeneous solution is obtained. The adduct Et₃SiH-AlCl₃ is then ready to use. Its concentration of Al is 1.086 mol/L.

Example 2.2

Preparation of the Adduct triethylsilane-AlCl₃-iPrOH

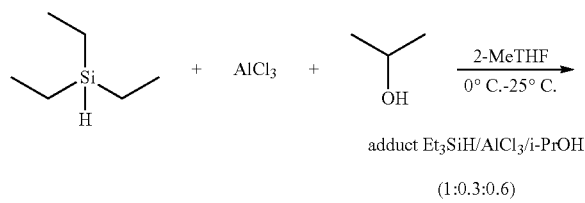

adduct Et₃SiH/AlCl₃/i-PrOH (1:0.3:0.6)

| Product | M | d | Mass (g) | n (mmol) | Vol. (mL) | Total vol. (mL) |
|---|---|---|---|---|---|---|
| AlCl₃ | 133.34 | — | 1.000 | 7.5 | — | — |
| 2-MeTHF | 86.13 | 0.860 | 5.375 | 62.4 | 6.250 | 6.250 |
| Et₃SiH | 116.28 | 0.728 | 2.912 | 25.0 | 4.000 | 10.250 |
| i-PrOH | 60.10 | 0.785 | 0.902 | 15.0 | 1.149 | 11.399 |

The 2-MeTHF is introduced into a 25 mL ground neck flask, equipped with a magnetic stirrer and internal thermometer. The 2-MeTHF is cooled to 0° C. by means of an ice bath, with stirring at 800 rpm (stirring maintained for the entire period of preparation of the adduct).

At 0° C., AlCl₃ is added in 10 portions at a rate of one portion every 3 minutes. After each addition, an increase in temperature of 5 to 8° C. is observed. When the temperature of the reaction mixture has returned to 0° C., a new addition can be performed. A clear pale yellow solution is obtained. Once the 10 additions have been performed, the temperature of the reaction medium is left to return to 25° C.

Et₃SiH is then added all at once with the aid of a syringe. The temperature remains stable at 25° C. The mixture obtained is stirred for 10 minutes at 25° C. The i-PrOH is then added all at once with the aid of a syringe. The temperature remains stable at 25° C. The mixture obtained is stirred for 30 minutes at 25° C. The mixture loses its colour progressively until it becomes very pale yellow. The clear solution of the adduct Et₃SiH/AlCl₃/i-PrOH (1:0.3:0.6) thus obtained is stored under argon at 25° C. and can be used in this form. The adduct can be stored for a number of months with no variation in its reactivity.

Example 3

Reduction of methyl Jasmonate by the Adduct PMHS-AlCl₃

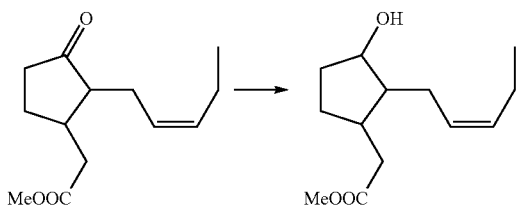 [SMILES: CC/C=C\CC1C(=O)CCC1CC(=O)OC ; CC/C=C\CC1C(O)CCC1CC(=O)OC]

1 h, 25° C.
Conversion: 95%
Selectivity: 93%

11.2 μL (0.05 mmol) of methyl jasmonate, 54 μL of adduct PMHS-AlCl₃ (prepared with 5 hydride equivalents produced from the PMHS) (54 μL correspond to 0.06 mmol of Al and 0.3 mmol of H⁻) are introduced into a flask equipped with a magnetic stirrer. The solution obtained is stirred at 25° C. for 1 h. 500 μL of an HCl$_{eq}$ 1 M solution are then introduced. The solution is stirred at 25° C. for 5 minutes, then extracted with ethyl ether. An analysis of the ethereal extract by GC/MS indicates a conversion of 95% of the initial cyclopentanone with a selectivity of 93% for the product resulting from the reduction of the C=O into CH—OH.

Example 4

Reduction of 4-14-hydroxyphenyl)but-3-en-2-one

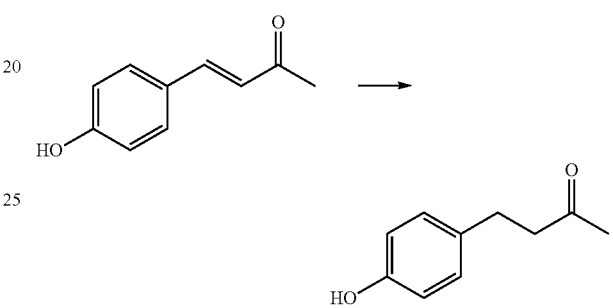

8.11 mg (0.05 mmol) of 4-(4-hydroxyphenyl)but-3-en-2-one, then 200 μL of Me-THF are introduced into a flask equipped with a magnetic stirrer. A clear yellow solution is obtained. 32.4 μL of the adduct PMHS-AlCl₃ (prepared with 1 hydride equivalent produced from the PMHS) (32.4 μL correspond to 0.05 mmol of Al and 0.05 mmol of H⁻) are then added to this solution. The solution obtained is stirred at 70° C. for 3 h. 500 μL of a solution HCl$_{eq}$ 1 M are then introduced. The solution is stirred for 5 minutes at 25° C., then extracted with ethyl ether. An analysis of the ethereal extract by GC/MS indicates a conversion of 94% of the initial enone and a selectivity of 73% for the 1,4 reduction product. The other products observed are 1,2 reduction products or double 1,4 and 1,2 reduction products or complete reduction products of the side chain into butyl radical.

The reduction of the 4-(4-hydroxyphenyl)but-3-en-2-one into frambinone was evaluated by comparing an adduct produced with aluminium trichloride and PMHS, an adduct produced with aluminium trichloride, and a mixture of aluminium trichloride and PMHS which were not pre-combined in the form of an adduct. The results obtained after 3 hours at 70° C. in 2-methyltetrahydrofuran are shown in table 1:

TABLE 1

| | Adduct PMHS-AlCl₃ | Adduct TMDS-AlCl₃ | PMHS and AlCl₃ not pre-combined |
|---|---|---|---|
| Conversion | 94% | 99% | 99% |
| Selectivity | 73% | 85% | 1% |

Thus, these results show that the use of a mixture of PMHS and aluminium trichloride leads to the formation of a complex mixture of products and that no selectivity for the ketone is observed.

The use of an adduct between aluminium trichloride and a hydrosilane leads to the formation of the saturated ketone with a very high yield and selectivity.

The adduct according to the present invention is thus especially effective for the selective reduction of ketones and α,β-unsaturated ketones, moreover selectively.

In addition to being very effective in terms of yield and selectivity, the PMHS-AlCl$_3$ adduct has also proven to be more suitable for handling in relaxed conditions, since it is stable in the presence of air and does not hydrolyse spontaneously, in contrast to AlCl$_3$, which has to be handled with care, under a hood, in a glovebox, is deliquescent and reacts violently with water.

Example 5

Reduction of 4-(4-hydroxyphenyl)but-3-en-2-one in the Presence of an Iodised Derivative The reduction of 4-(4-hydroxyphenyl)but-3-en-2-one was also repeated in the conditions of example 3 with a triethylsilane/ammonium trichloride adduct in the presence of an iodised derivative (either CuI or iodine I$_2$) or in the presence of an alcohol (iso-propanol).

The results are shown in table 2:

TABLE 2

| | Period | Adduct Et$_3$SiH—AlCl$_3$ (1:0.3) | Adduct Et$_3$SiH—AlCl$_3$—CuI (1:0.3:1.2) | Adduct Et$_3$SiH—AlCl$_3$—I$_2$ (1:0.3:1.2) | Adduct Et$_3$SiH—AlCl$_3$—iPrOH (1:0.3:0.9) |
|---|---|---|---|---|---|
| Conversion | 1 h | | 86% | | >98% |
| | 2 h | 92% | | | |
| | 3 h | | 98% | 91% | |
| Selectivity | 1 h | | 97% | | >96% |
| | 2 h | 91% | | | |
| | 3 h | | 92% | 100% | |

The adduct between aluminium trichloride and triethylsilane makes it possible to obtain the saturated ketone with an increased selectivity.

The selectivity of the 1,4 reduction can be further increased if the adduct Et$_3$SiH/AlCl$_3$ is used in the presence of cuprous iodide, iodine, or iso-propanol.

The use of the adduct according to the present invention in the presence of an iodised derivative or an alcohol such as iso-propanol makes it possible to completely control the reduction of an α,β-unsaturated ketone in position β.

The same reaction can be performed with an adduct between iron trichloride and a hydrosilane, especially triethylsilane. The results with iron trichloride and aluminium trichloride are summarised in table 3:

TABLE 3

| Entry | Adduct | t (h) | Conv. (%) | Select. (%) |
|---|---|---|---|---|
| 1 | TES-AlCl$_3$—i-PrOH (1:0.3:0.6) | 2 h | 98 | 96 |
| 2 | TES-FeCl$_3$ (1:1) | 3 h | 100 | 78 |
| 3 | TES-FeCl$_3$ (1:0,.) | 3 h | 96 | 88 |
| 4 | TES-FeCl$_3$—i-PrOH (1:0.3:0.6) | 2 h | 90 | 94 |
| 5 | TES-FeCl$_3$ not preformed (1:1) | 2 h | <90 | <78 |

The reaction can be carried out on a large scale (10 g) with a similar conversion and selectivity (98% conversion and 99% selectivity).

These reaction conditions can be used with the compounds of formula IIa1a, especially selected from those in which R$_{15}$ is methoxy, R$_{16}$ is OH and R$_{17}$ is methyl; R$_{15}$ is ethoxy, R$_{16}$ is OH and R$_{17}$ is methyl; R$_{15}$ is n-propoxy, R$_{16}$ is OH and R$_{17}$ is methyl; R$_{15}$ is i-propoxy, R$_{16}$ is OH and R$_{17}$ is methyl; R$_{15}$ is n-butoxy, R$_{16}$ is OH and R$_{17}$ is methyl; R$_{15}$ is i-butoxy, R$_{16}$ is OH and R$_{17}$ is methyl; and R$_{15}$ is t-butoxy, R$_{16}$ is OH and R$_{17}$ is methyl.

Additional tests aimed at improving the reaction conditions and/or the reactivity with the adduct of FeCl$_3$ were also performed.

Example 5.1

Modification of the Solvent

The reduction of the 4-(4-hydroxyphenyl)but-3-en-2-one is repeated with the adduct TES-FeCl3-i-PrOH (1:0.3:0.6). The results are compiled in table 4.

TABLE 4

| Entry | Solvent | Time | Temperature | Conv. (%) | Select. (%) |
|---|---|---|---|---|---|
| 1 | MeTHF | 4 h | 50° C. | 34 | 100 |
| 2 | MeTHF | 2 h | 80° C. | 96 | 82 |

TABLE 4-continued

| Entry | Solvent | Time | Temperature | Conv. (%) | Select. (%) |
|---|---|---|---|---|---|
| 3 | AcOEt | 4 h | TA | 66 | 98 |
| 4 | AcOEt | 4 h | 30° C. | 91 | 78 |
| 5 | AcOEt | 2 h | 50° C. | 94 | 82 |

The choice of ethyl acetate as solvent promotes the selective reduction of 4-(4-hydroxyphenyl)but-3-en-2-one.

Example 5.2

Reduction of the Iron Catalytic Burden

Additional tests aimed at reducing the amount of FeCl$_3$ were performed.

| Entry | FeCl$_3$ | Sol%%vent | Temperature | Conv. (%) | Select. (%) |
|---|---|---|---|---|---|
| 1 | 20% | Me-THF | 70° C. | 99 | 92 |
| 2 | 10% | Me-THF | 70° C. | 83 | 95 |
| 3 | 5% | Me-THF | 70° C. | 16 | 100 |
| 4 | 20% | AcOEt | 70° C. | 94 | 83 |
| 5 | 10% | AcOEt | 50° C. | 96 | 80 |
| 6 | 10% | AcOEt | 70° C. | 97 | 77 |
| 7 | 5% | AcOEt | 50° C. | 55 | 99 |
| 8 | 5% | AcOEt | 70° C. | 90 | 88 |

The amount of iron can be reduced to 5% relative to the amount of substrate whilst maintaining a high conversion and selectivity.

Example 5.3

Post-Reaction Treatment

The conditions for isolating the crude reaction product have also been the topic of studies. The isolation of the product is made difficult by the presence of silylated residues and the nature of the product (phenol).

| | |
|---|---|
| HCl 1M | Loss of product (too acidic) |
| MeOH/NaOH 2M | Loss of product (too alkaline) |
| MeOH/NaOH 1M, 0.5M or 0.1M | Hydrolysis by-products |
| MeOH/K$_2$CO$_3$ | Loss of product (too alkaline) |
| MeOH/KOH 4M | Loss of product (too alkaline) |
| NH$_4$OH 10% mol | Hydrolysis by-products |
| MeOH/H$_2$O/NaF | Hydrolysis by-products |
| MeOH/NaF | Hydrolysis by-products |
| MeOH/NaHCO$_3$ sat. | Clean, no loss of product |

The selected treatment conditions are thus a weakly alkaline solution during hydrolysis. The standard procedure for 0.4 mmol of hydrosilane used is as follows: MeOH (1 ml) added to the base (example: NaHCO$_3$) (10 ml) is added to the reaction mixture. The resulting mixture is stirred at ambient temperature for 3 h, then extracted with dichloromethane Ch$_2$Cl$_2$ (3×20 ml). The organic phases are collected then dried over MgSO$_4$ and the solvent is removed under reduced pressure. The crude product is filtered over silica or dicalite.

Example 6

Preparation of an Ether from Cyclohexanone

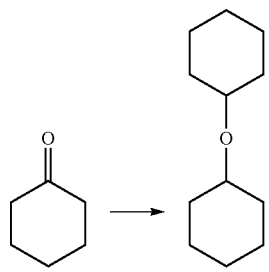 [SMILES: O=C1CCCCC1 ; C1CCC(OC2CCCCC2)CC1]

3.9 mg (4 mmol) of cyclohexanone are added to the adduct triethylsilane-AlCl$_3$ of example 2 and the solution is stirred at ambient temperature for 3 hours. At the end of the reaction, dicyclohexyl ether is obtained with a selectivity of 100%.

Example 7

Preparation of Cyclopentyl Methyl Ether

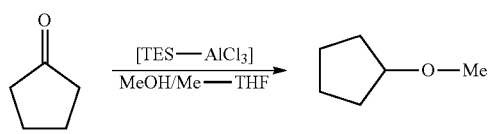

Cyclopentanone (0.1 mmol; 8.9 mL) is diluted in an equivalent of methanol and 40 μL of Me-THF. [TES-AlCl$_3$] (1:1; (1 equivalent) prepared in Me-THF is added in 2 stages to the cyclopentanone. After 2 hours at 80° C., a total conversion of the cyclopentanone was obtained. 56% of CPME are obtained.

Example 8

Reduction of Pulegone

It is possible to selectively reduce the 1,4 position with the aid of the system [TES-AlCl$_3$]. The addition of CuI, of I$_2$, or of iso-propanol, or of zinc dichloride to the adduct [TES-AlCl$_3$-iPrOH], or of tert-butanol makes it possible to increase the selectivity in favour of position 4. The selectivity is total with the adducts [TES-AlCl$_3$-iPrOH+ZnCl$_2$] and above all [TES-AlCl$_3$-tBuOH].

It is preferable to carry out the reaction without addition of solvent other than that which is already present in the adduct.

It is also possible to chain the reduction of the 1,4 then 1,2 positions so as to obtain menthol. This further reduction then requires the use of the adduct [TES-AlCl$_3$] in excess (3 equivalents).

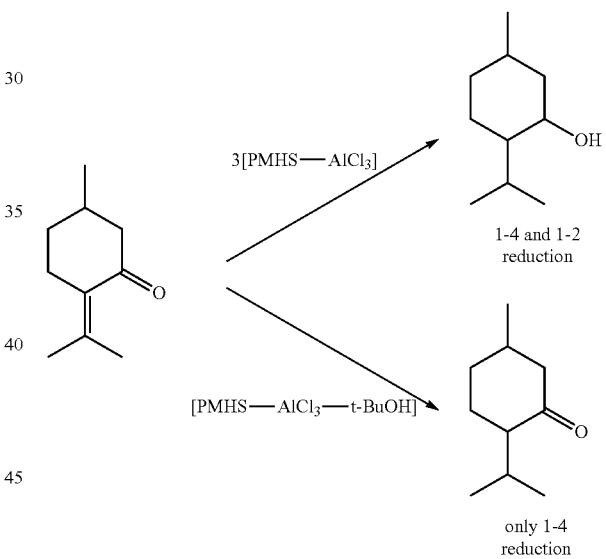

Example 9

Reduction of Pulegone into Menthone

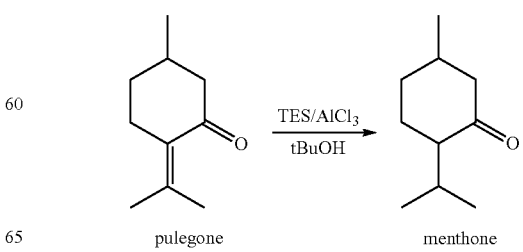

8.2 µL (0.05 mmol) of pulegone are added to the adduct [TES-AlCl$_3$-tBuOH] (molar ratio 1:0.3:0.6) or [TES-AlCl$_3$-iPrOH-ZnCl$_2$] (molar ratio 1:0.3:0.6:1) prepared in methyl-THF, and the solution is stirred at 80° C. for 3 hours. At the end of the reaction, the menthone is obtained with a selectivity of 92% and a yield of 73%. No trace of ether is observed.

With the adduct PMHS/FeCl$_3$/iPrOH (3:0.3:0.6), menthone is obtained with a yield of 83% and a selectivity of 67%.

The results of the reduction of pulegone with iron trichloride and aluminium trichloride are summarised in table 5:

TABLE 5

| Entry | Adduct | t (h) | Product | Conv. (%) | Select. (%) |
|---|---|---|---|---|---|
| 1 | PMHS-AlCl$_3$ (1:1) | 2 h | menthone | 78 | 72 |
| 3 | PMHS-AlCl$_3$—i-PrOH (3:0.3:0.6) | 2 h, 90° C. | menthol | 100 | 70 |
| 4 | TES-AlCl$_3$—i-PrOH (3:0.3:0.6) | 4 h | menthone | 96 | 90 |
| 5 | 1) TES-AlCl$_3$—i-PrOH (3:0.3:0.6) 2) TES-FeCl$_2$ (1:1) in situ | 2 h | menthone | 100 | 90 |
| 6 | 1) TES-AlCl$_3$—i-PrOH (1:0.3:0.6) 2) ZnCl$_2$ (1 equiv) | 5 h, 90° C. | menthone | 99 | 90 |
| 7 | TES-AlCl$_3$—EtOH (3:0.3:0.6) | 3 h | menthone | 94 | 61 |
| 8 | TES-FeCl$_3$—i-PrOH (3:0.3:0.6) | 3 h | menthol | 100 | 28 |
| 9 | PMHS-FeCl$_3$—i-PrOH (3:0.3:0.6) | 3 h | menthone | 83 | 67 |

It is important to note that the adducts PMHS-AlCl$_3$-i-PrOH (3:0.3:0.6) and TES-FeCl$_3$-i-PrOH (3:0.3:0.6) enable one-pot preparation of menthol from pulegone.

Example 10

Preparation of 2-pentylcyclopentanone

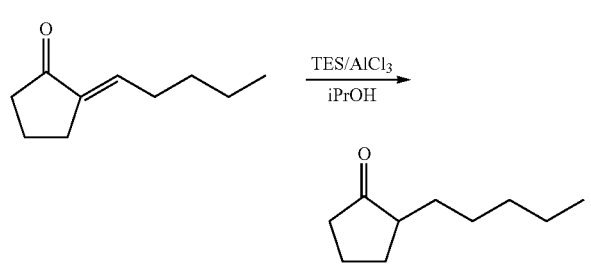

8.2 µL (0.05 mmol/1 equivalent/TES) of enone are added to the adduct triethylsilane-AlCl$_3$-iPrOH (molar ratio 1:0.3:0.6) prepared in cyclopentyl methyl ether and the solution is stirred at 80° C. for 3 hours. At the end of the reaction, 2-pentylcyclopentanone is obtained with a selectivity of 100%. No trace of ether or of cyclopentanol is observed.

The same reaction, performed with an adduct triethylsilane-FeCl$_3$-iPrOH (molar ratio 1:0.3:0.6), triethylsilane-FeCl$_3$-iPrOH (molar ratio 2:0.3:0.6), triethylsilane-FeCl$_3$-iPrOH (molar ratio 1:0.5:0.6) or an adduct triethylsilane-FeCl$_3$ (molar ratio 2:0.3) leads to the formation of 2-pentylcyclopentanone with a conversion of 67, 84, 78 and 80% and a selectivity for the ketone greater than 90%.

The results with the adducts of iron trichloride and aluminium trichloride are summarised in table 6:

| Adduct | Conv. (%) | Select. (%) | Conv. (%) | Select. (%) | t(h) |
|---|---|---|---|---|---|
| TES-AlCl$_3$—i-PrOH (1:0.3:0.6) | 74 | 97 | 87 | 100 | 4 h |
| TES-FeCl$_3$—i-PrOH (1:0.3:0.6) | 18 | 100 | 67 | 100 | 3 h |
| TES-FeCl$_3$—i-PrOH (2:0.3:0.6) | 70 | 100 | 84 | 90 | 3 h |
| TES-FeCl$_3$—i-PrOH (1:0.5:0.6) | 7 | 93 | 78 | 100 | 3 h |
| TES-FeCl$_3$ (1:0.3) | 5 | nd | 80 | 100 | 4 h |
| TES-FeCl$_3$ (2:0.3) | 63 | 100 | 80 | 100 | 4 h |

Example 11

Preparation of Cyclohexanol from Cyclohexanone

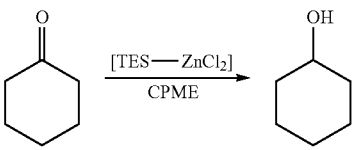

4.9 mg (0.05 mmol, 1 equivalent/TES) of cyclohexanone are added to the adduct triethylsilane-ZnCl$_2$ (molar ratio 1:1) prepared in 50 µL cyclopentyl methyl ether and the solution is stirred at 90° C. for 4 hours. At the end of the reaction, cyclohexanol is obtained with a selectivity of 100%.

Example 12

Preparation of 2-dodecanol by Reduction of 2-dodecacone

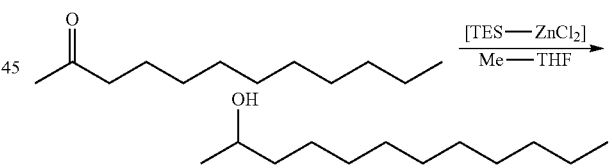

11.2 µL (0.05 mmol, 1 equivalent/TES) of cyclohexanone are added to the adduct triethylsilane-ZnCl$_2$ (molar ratio 1:1) prepared in 50 µL of cyclopentyl methyl ether and the solution is stirred at 90° C. for 3 hours. At the end of the reaction, cyclohexanol is obtained with a selectivity of 100% and a conversion rate of 75%. No trace of ether or of dodecane is observed.

The invention claimed is:

1. A pre-formed adduct between a Lewis acid selected from the salts of zinc (II), tin (II) or (IV), iron (II) or iron (III), copper (I), palladium (II), titanium (III) or (IV), bismuth (III) or aluminium (III) and a hydrosilane.

2. The adduct according to claim 1, wherein the Lewis acid is a salt of zinc (II), a salt of iron (III), or a salt of aluminium (III).

3. The adduct according to claim 1, wherein the hydrosilane is selected from the group selected from consisting of trialkylsilanes, tris(trimethylsilyl)silane, triphenylsilane, polymethylhydrosiloxanes (PMHS), polydimethylsiloxanes having a terminal Si—H group, a methylhydro-dimethylsiloxane copolymer, a methylhydrophenyl-methylsiloxane copolymer, a methylhydrocyanopropylsiloxane copolymer, a methylhydromethyloctylsiloxane copolymer, poly(1,2-dimethylhydrosilazane), a 1-methyl-hydrosilazane (1,2-dimethylhydrosilazane) copolymer, and methylhydrocyclosiloxane.

4. The adduct according to claim 3, wherein the hydrosilane is selected from the group consisting of polymethylhydrosiloxane, tetramethyldisiloxane and triethylsilane.

5. The adduct according to claim 1, further comprising another Lewis acid, a metal salt, an alcohol, or a dihalogen.

6. The adduct according to claim 5, comprising an alcohol.

7. An adduct $AlCl_3$ /triethylsilane/isopropanol in a molar ratio of 0.3:1:0.6.

8. An adduct $FeCl_3$ /triethylsilane/iso-propanol or $FeCl_3$ /triethylsilane /tert-butanol in a molar ratio of x:1:2x, where X varies from 0.01 to 1.

9. A method for performing a reaction of reduction of an aldehyde, an α,β-unsaturated aldehyde, a ketone, an α,β-unsaturated ketone, an imine, or an α,β-unsaturated imine, comprising providing the adduct of claim 1, and combining the adduct with the aldehyde, α,β-unsaturated aldehyde, ketone, α,β-unsaturated ketone, imine, or α,β-unsaturated imine.

10. The method according to claim 9, wherein the reduction is of a ketone or an α,β-unsaturated ketone.

11. The method according to claim 9, wherein the reduction is of a ketone, an α,β-unsaturated ketone, an imine, or an α,β-unsaturated imine of formula (Ia):

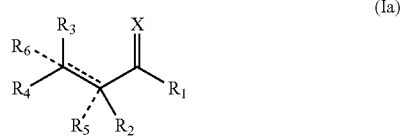

(Ia)

in which:
X is O or N $R_a$, $R_a$ being selected from the group consisting of a linear or branched alkyl having at most 12 carbon atoms, a linear or branched alkylene having at most 6 carbon atoms, a carbocyclic or heterocyclic aryl, and an aralkyl radical, each of said alkyl, alkylene, aralkyl or aryl radicals being optionally substituted,
=== is a single bond or a double bond,
$R_1$ is a linear or branched alkyl radical having at most 12 carbon atoms, a linear or branched alkylene having at most 12carbon atoms, or a saturated or unsaturated cycloalkyl radical having 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl or aryl radicals being optionally substituted,
$R_2$ is hydrogen, linear or branched alkyl having at most 12 carbon atoms, a linear or branched alkylene having at most 6carbon atoms, a carbocyclic or heterocyclic aryl, or an aralkyl radical, each of said alkyl, alkylene, aralkyl or aryl radicals being optionally substituted,
$R_3$ and $R_4$, which are identical or different, are hydrogen, a linear or branched alkyl having at most 12 carbon atoms, a linear or branched alkylene having at most 6 carbon atoms, a carbocyclic or heterocyclic aryl, or an aralkyl radical, each of said alkyl, alkylene, aralkyl or aryl radicals being optionally substituted, and when === is a single bond,
$R_5$ is hydrogen, a linear or branched alkyl having at most 12 carbon atoms, a linear or branched alkylene having at most 12 carbon atoms, a carbocyclic or heterocyclic aryl, or an aralkyl radical, each of said alkyl, alkylene, aralkyl or aryl radicals being optionally substituted, and
$R_6$ is hydrogen, a linear or branched alkyl having at most 12 carbon atoms, a linear or branched alkylene having at most 12 carbon atoms, a carbocyclic or heterocyclic aryl, or an aralkyl radical, each of said alkyl, alkylene, aralkyl or aryl radicals being optionally substituted,
or a cyclic ketone, α, β-unsaturated ketone, imine or α, β-unsaturated imine of formula (Ib):

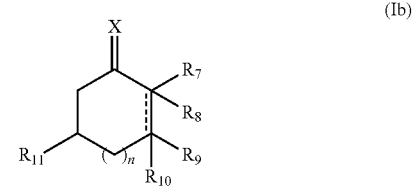

(Ib)

in which:
n =0 or 1,
X and === are as defined above,
$R_7$ is a linear or branched alkyl radical having at most 12 carbon atoms, a linear or branched alkylene having at most 12carbon atoms, or a saturated or unsaturated cycloalkyl radical having 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl, aryl or cycloalkyl radicals being optionally substituted,
$R_9$ is a hydrogen, a linear or branched alkyl radical having at most 12 carbon atoms, a linear or branched alkylene having at most 12 carbon atoms, or a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl or aryl radicals being optionally substituted, or a $CHR_{12}$—$COOR_{13}$ group, in which $R_{12}$ is hydrogen or a linear or branched alkyl radical having at most 12 carbon atoms, and $R_{13}$ is a linear or branched alkyl radical having at most 12 carbon atoms or a saturated or unsaturated cycloalkyl radical having from 3 to 7 carbon atoms, and optionally comprising one or more heteroatoms selected from nitrogen, sulfur or oxygen atoms, a carbocyclic aryl radical, an aralkyl radical, each of said alkyl, alkylene, aralkyl or aryl radicals being optionally substituted, and
when === is a single bond,
$R_8$, and $R_{10}$, which are identical or different, are a hydrogen, a linear or branched alkyl radical having at most 12carbon atoms, a linear or branched alkylene having at most 12carbon atoms, or a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl or aryl radicals being optionally substituted, or a $CHR_{12}$—$COOR_{13}$ group, in which $R_{12}$ is hydrogen or a linear or branched alkyl radical having at most 12 carbon atoms, and $R_{13}$ is a linear or branched alkyl radical having at most 12 carbon atoms or a saturated or unsaturated cycloalkyl radical having from 3 to 7 carbon atoms, and optionally comprising one or more heteroatoms selected from nitrogen, sulfur or oxygen atoms, a carbocyclic aryl radical, $R_{11}$ is hydrogen, a linear or branched alkyl radical having at most 12 carbon atoms, a linear or branched alkylene having at most 12 carbon atoms, or a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl or aryl radicals being optionally substituted, advantageously an alkyl radical having at most 12 carbon atoms, or, when ═══ is a single bond, $R_7$ and $R_8$ are together a ═CH—$R_{7a}$ group where $R_{7a}$ is hydrogen, a linear or branched alkyl radical having at most 11 carbon atoms, or a saturated or unsaturated cycloalkyl radical having from 3 to 7 carbon atoms and optionally comprising one or more heteroatoms selected from nitrogen, sulfur or oxygen atoms, a carbocyclic or heterocyclic aryl radical, an aralkyl radical, each of said alkyl, alkylene, aralkyl or aryl radicals being optionally substituted, or for the reduction of a compound of the following formula (IV):

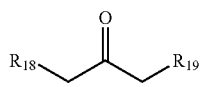

in which $R_{18}$ and $R_{19}$ are, independently of one another, an optionally substituted linear or branched alkyl radical having at most 11 carbon atoms, $R_{18}$ and $R_{19}$ are linked together to form a saturated or unsaturated cycloalkyl radical having from 3 to 7 carbon atoms and optionally comprising one or more heteroatoms selected from nitrogen, sulfur or oxygen atoms.

12. A method for preparing a compound of formula (IIIb):

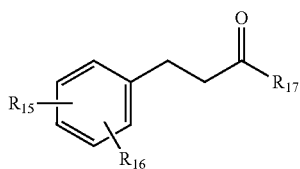

in which:
$R_{15}$ and $R_{16}$ are, independently of one another, hydrogen, an optionally substituted linear or branched alkyl radical having at most 12 carbon atoms, an optionally substituted linear or branched alkylene radical having at most 12 carbon atoms, an optionally substituted linear or branched alkoxy radical having at most 12 carbon atoms, OH, $COOR_{13}$ where $R_{13}$ is a linear or branched alkyl radical having at most 12 carbon atoms, a saturated or unsaturated cycloalkyl radical having from 3 to 7 carbon atoms, $CF_3$, halogen selected from F, Cl, Br and I, said substituents $R_{15}$ and $R_{16}$ being positioned in the ortho, meta or para position of the ring, $R_{17}$ is a linear or branched alkyl radical having at most 12 carbon atoms, comprising a step of contacting a compound of formula (IIa)

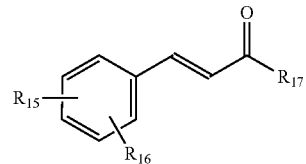

with an adduct according to claim 1.

13. A method according to claim 12, in which the compound of the following formula (IIIa1):

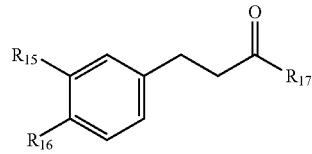

in which $R_{15}$ and $R_{16}$, independently of one another, are an optionally substituted linear or branched alkoxy radical having at most 12 carbon atoms, or OH, $R_{17}$ is a linear or branched alkyl radical having at most 12 carbon atoms, comprising a step of contacting a compound of formula (IIa1)

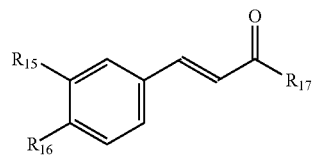

with an adduct according to claim 1.

14. A method for preparing a compound of the following compound (IIIb):

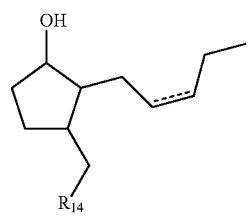

in which:
═══ is a single bond or a double bond,
$R_{14}$ is hydrogen, a linear or branched alkyl radical having at most 11 carbon atoms, a linear or branched alkylene having at most 11 carbon atoms, or a $COOR_{13}$ group where $R_{13}$ is a linear or branched alkyl radical having at most 12 carbon atoms, a saturated or unsaturated cycloalkyl radical having from 3 to 7 carbon atoms, comprising a step of contacting a compound of formula (IIb)

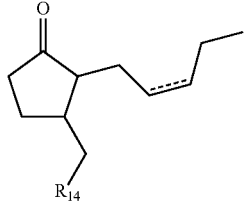

with an adduct according to any claim 1.

15. A method for preparing a dialkylether of the following formula (V):

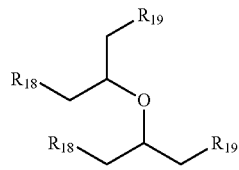

in which $R_{18}$ and $R_{19}$ are, independently of one another, an optionally substituted linear or branched alkyl radical having at most 11 carbon atoms, or $R_{18}$ and $R_{19}$ are linked together to form a saturated or unsaturated cycloalkyl radical having from 3 to 7 carbon atoms and optionally comprising one or more heteroatoms selected from nitrogen, sulfur or oxygen atoms, comprising a step of contacting a compound of the following formula (IV):

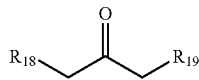

with an adduct according to claim 1.

16. A method for preparing a dicycloalkylether of the following formula (Va):

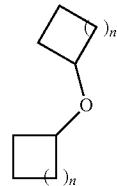

in which n =1 to 4, and optionally comprising one or more heteroatoms selected from nitrogen, sulfur or oxygen atoms, comprising a step of contacting a cyclic ketone of the following formula (IVa):

with an adduct according to claim 1.

17. The adduct according to claim 2, wherein the hydrosilane is selected from the group consisting of trialkylsilanes, tris(trimethylsilyl)silane, triphenylsilane, polymethylhydrosiloxanes (PMHS), polydimethylsiloxanes having a terminal Si—H group, a methylhydro-dimethylsiloxane copolymer, methylhydrophenyl-methylsiloxane copolymer, a methylhydrocyanopropylsiloxane copolymer, a methylhydromethyloctylsiloxane copolymer, poly(1,2-dimethylhydrosilazane) a 1-methyl-hydrosilazane) (1,2-dimethylhydrosilazane) copolymer, and methylhydrocyclosiloxane.

18. The adduct according to claim 2, further comprising another Lewis acid, a metal salt, an alcohol, or a dihalogen.

19. The adduct according to claim 3, further comprising another Lewis acid, a metal salt, an alcohol, or a dihalogen.

20. The adduct according to claim 4, further comprising another Lewis acid, a metal salt, an alcohol, or a dihalogen.

21. The adduct according to claim 2, wherein the Lewis acid is a salt of zinc dichloride, a salt of iron trichloride, or a salt of aluminium trichloride.

22. The adduct according to claim 6, comprising isopropanol or tert-butanol.

23. The adduct according to claim 6 comprising an alcohol in a molar ratio of Lewis acid/alcohol of 1:2.

24. The adduct according to claim 8, where x varies from 0.05 to 0.3.

* * * * *